(12) United States Patent
Scheuermann et al.

(10) Patent No.: US 6,325,772 B1
(45) Date of Patent: Dec. 4, 2001

(54) ORTHESIS FOR IMMOBILIZING THUMB BASE JOINT

(75) Inventors: Rainer Scheuermann, Kiel; Holger Reinhardt; Hans Bruno Bauerfeind, both of Kempen, all of (DE)

(73) Assignee: Bauerfeind Orthopadie GmbH & Co. KG (DE)

(*) Notice: Subject to any disclaimer, the term of this patent is extended or adjusted under 35 U.S.C. 154(b) by 0 days.

(21) Appl. No.: 09/202,957

(22) PCT Filed: Jun. 24, 1997

(86) PCT No.: PCT/EP97/03312

§ 371 Date: Sep. 1, 1999

§ 102(e) Date: Sep. 1, 1999

(87) PCT Pub. No.: WO97/49358

PCT Pub. Date: Dec. 31, 1997

(51) Int. Cl.$^7$ .................. A61F 5/00; A61F 13/00
(52) U.S. Cl. .................. 602/22; 602/60; 602/61; 602/64
(58) Field of Search .................. 602/5, 20, 21, 602/22, 60, 61, 62, 64; 2/21, 159, 161.1, 161.3, 161.6, 161.7, 161.8; D24/190

(56) References Cited

U.S. PATENT DOCUMENTS

| | | | |
|---|---|---|---|
| D. 373,639 | * | 9/1996 | McKie .................. D24/190 |
| D. 405,180 | * | 2/1999 | Reina .................. D24/190 |
| 2,388,330 | | 11/1945 | Jungmann . |
| 5,397,296 | | 3/1995 | Sydor et al. . |
| 5,554,107 | * | 9/1996 | Shannahan .................. 602/66 |
| 5,873,130 | * | 2/1999 | Lafferty .................. 2/16 |
| 5,928,172 | * | 7/1999 | Gaylord .................. 602/21 |
| 6,093,165 | * | 7/2000 | Estwanik .................. 602/64 |
| 6,098,200 | * | 8/2000 | Minkow et al. .................. 2/161.1 |
| 6,119,267 | * | 9/2000 | Pozzi .................. 2/20 |
| 6,142,966 | * | 11/2000 | Hely .................. 602/64 |

FOREIGN PATENT DOCUMENTS

| | | |
|---|---|---|
| 30 06 362 A | 8/1981 | (DE) . |
| 36 31 253 | 3/1988 | (DE) . |
| 88 06 792 U | 10/1988 | (DE) . |
| 42 18 594 A | 12/1993 | (DE) . |

* cited by examiner

*Primary Examiner*—Kim M. Lewis
(74) *Attorney, Agent, or Firm*—Banner & Witcoff, Ltd.

(57) ABSTRACT

The invention concerns an orthesis, made of flexible material, for immobilizing the thumb base joint, with a wrist strap surrounding the wrist and with a tubular extension piece receiving the thumb. The extension piece contains a sheathlike reinforcement with a transverse cutout located on the inside of the thumb base joint, and has in the region of the thumb base joint, on the outside of the thumb, a transverse slit of a length such that the transverse slit opens when the thumb base joint is bent, the degree of opening being limited by a flap which, bridging the transverse slit, extends from the outer region of the extension piece to the wrist strap and can be secured to the latter.

7 Claims, 3 Drawing Sheets

ORTHESIS FOR IMMOBILIZING THUMB BASE JOINT

This application is based upon an International Application No. PCT/EP97/03312, filed Jun. 24, 1997.

The invention relates to an orthesis, made of flexible material, for immobilizing the thumb base joint, with a wrist strap surrounding the wrist and with a tubular extension piece receiving the thumb.

An orthesis of this type is known from DE-A-36 31 253. This orthesis serves, in particular, for absorbing high loads on the hand, such as occur, for example, in some types of ball sports and in heavy manual activity. For this purpose, the orthesis contains a flexible barlike supporting element in the region of the tubular thumb extension piece. This supporting element is also intended to provide support for the thumb base joint in the case of injuries in the region of the latter.

A similar orthesis is described in U.S. Pat. No. 2,388,330, in which a half shell, with a flap capable of being secured to the thumb, is provided instead of the tubular thumb extension piece, the half shell being fastened to the wrist via elastic steel springs.

The object of which the invention is based is to provide an orthesis according to the information given above, which allows therapy adapted to the given conditions of an injury. This object is achieved, according to the invention, in that the extension piece contains a sheathlike reinforcement, with a transverse cutout located on the inside of the thumb base joint, and has in the region of the thumb base joint, on the outside of the thumb, a transverse slit of a length such that the transverse slit opens when the thumb base joint is bent, the degree of opening being limited by a flap which, bridging the transverse slit, extends from the outer region of the extension piece to the wrist strap and can be secured to the latter. Since the possibility of bending the thumb base joint is limited by the respective position of the flap, it is possible, depending on diagnosis, to establish a mobility of the thumb base joint which is limited to a greater or less extent, the securing of the flap bridging the transverse slit determining whether, on the one hand, the opening of the slit is prevented completely, that is to say the thumb base joint is not given any possibility of movement, or, on the other hand, the securing of the flap allows the slit to open to a greater extent, thus making it possible for the thumb base joint to bend correspondingly. Within these limits, it is possible, merely by securing the flap selectively to the wristband, to determine whether at all or to what extent the patient can move his thumb base joint, whilst, even during the period of treatment, this treatment can be adapted to the patient's respective state, specifically, where appropriate, by giving the thumb base joint an increasing possibility of movement. In this case, because of the sheathlike reinforcement in the extension piece, the thumb base joint continues to be supported against any undesirable lateral flexion which, in the case of an injury of the side ligaments of the thumb base joint, would be possible and is prevented by the sheathlike reinforcement. However, the latter allows the thumb base joint to bend to an extent which is desired where appropriate, since, in this case, this bending is limited, depending on the securing of the flap to the wristband, the transverse cutout in the sheathlike reinforcement being pushed together correspondingly on the inside of the thumb base joint, so that, therefore, the sheathlike reinforcement, on the one hand, allows the necessary transverse stabilization of the thumb base joint and, on the other hand, because of the presence of the transverse slit and inner cutout, permits therapeutically adapted bending of the thumb base joint.

The wrist strap is expediently provided, on its outside, with a coating of fleecy material of a touch-and-close fastening and the flap, on its inside, with the hooked material for selective securing to the wrist strap. By virtue of the fleecy material, the orthesis thereby acquires outwardly a soft outer surface which is agreeable to the wearer and to which the flap can then be secured by means of the hooked material attached on its inside. Since it is possible, at the same time, for the flap to be selectively secured to a greater or lesser extent in the vicinity of the transverse slit, a corresponding degree of opening of the latter is obtained, with the result that securing the flap to the wrist strap also makes it possible to establish the degree of possible movement and achieve a corresponding therapeutic effect.

In order, at the same time, essentially to define this latitude of movement, the wrist strap, together with the extension piece, and the flap are expediently designed in such a way that they consist of essentially nonstretchable material. It is also possible, however, to produce the flap from elastic material, so that an additional therapeutic effect can thereby be achieved.

In order to connect the tubular extension piece and the wrist strap to one another in a stable manner, the reinforcement is expediently designed in such a way that it extends into the wrist strap which is covered, on its outside, with the fleecy material and, on its inside, with a textile material. This makes it possible for the orthesis to be worn with a good degree of comfort.

In order to make it easier to put on the orthesis, in particular adapted to hands of different size, the wrist strap is expediently designed in such a way that it terminates in a touch-and-close fastening. The latter can comfortably be adapted to any wrist of a patient. So that the wrist strap can, at the same time, be put on particularly firmly, it is expediently designed in such a way that it contains a belt which can be secured selectively to the wrist strap by means of an eyelet passing through said wrist strap.

An exemplary embodiment of the invention is illustrated in the figures, of which:

Figure 1:
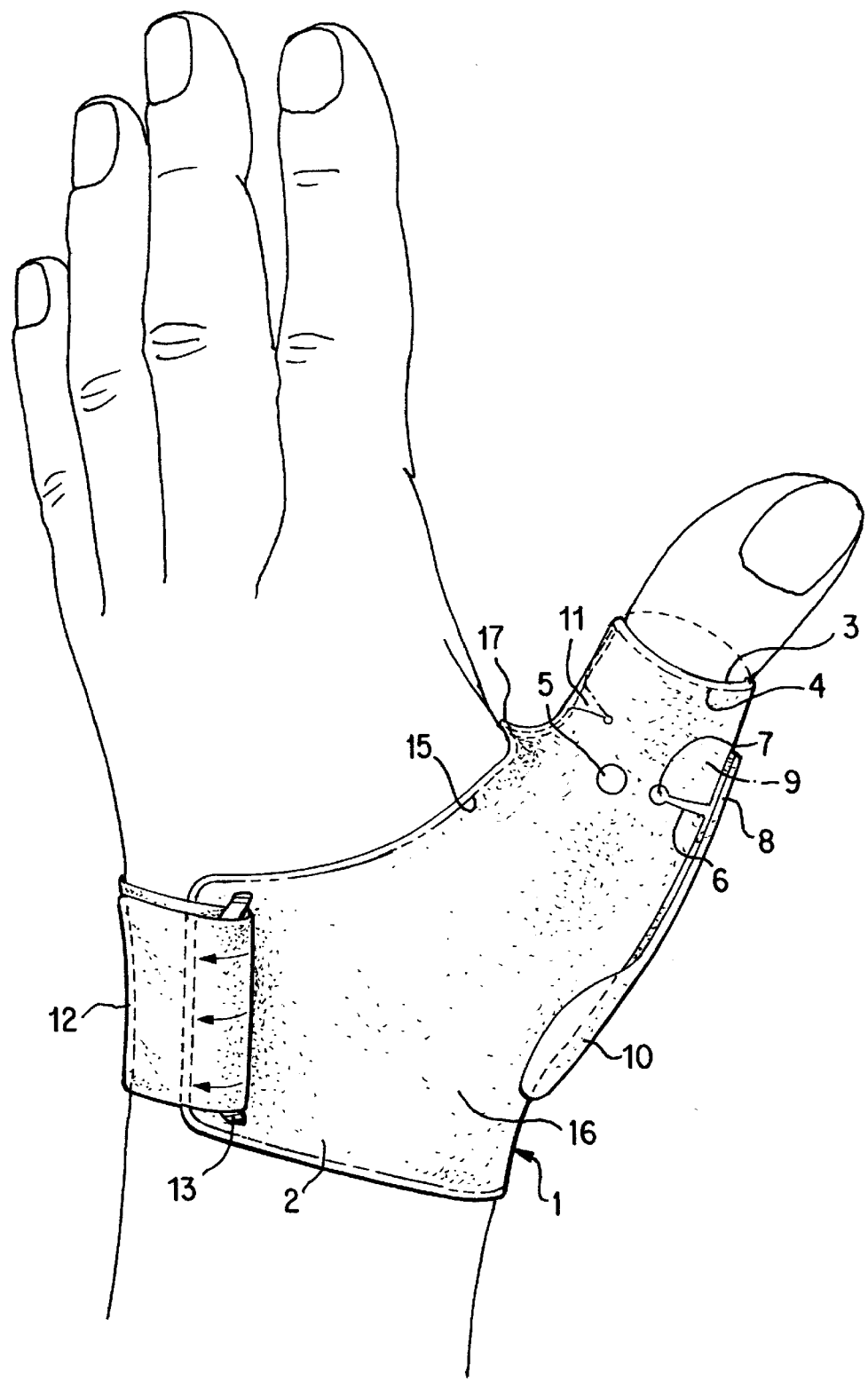
FIG. 1 shows a perspective view of the orthesis attached to a left hand.

In FIG. 1, the orthesis 1 is illustrated, attached to the left hand of a patient. The orthesis 1 consists of the wrist strap 2 which loops round the wrist and which is secured to the latter in a way described further below. The wrist strap 2 merges into the tubular extension piece 3 receiving the thumb. The extension piece 3 contains a sheathlike reinforcement 4 which is adapted to it and extends into the region 16 of the wrist strap 2 and the contours of which are indicated by the dashed and dotted line 15. In the region of the thumb base joint, indicated by the circle 5, the extension piece 3 has the transverse slit 6 which terminates in the rounding 7 in order to avoid tears. The transverse slit 6 passes altogether through the extension piece 3 and therefore, of course, also the reinforcement 4. With the thumb in the position illustrated, the transverse slit 6 is virtually closed, since FIG. 1 shows the thumb with its thumb base joint in the elongated position. A flap 8 is fastened above the transverse slit 6, as indicated by the dashed and dotted line 9 passing through the flap 8. The flap 8 extends over the transverse slit 6 as far as the wrist strap 2 and can be secured to the latter in the way explained further below.

When it is desired, then, to give the thumb some latitude of movement in the region of its thumb base joint 5, the flap 8 is fastened with its selectively securable end 10 to the wrist strap 2 in such a way that the transverse slit 6 can open when the thumb is moved. This is explained further below in connection with FIG. 3.

Figure 2:
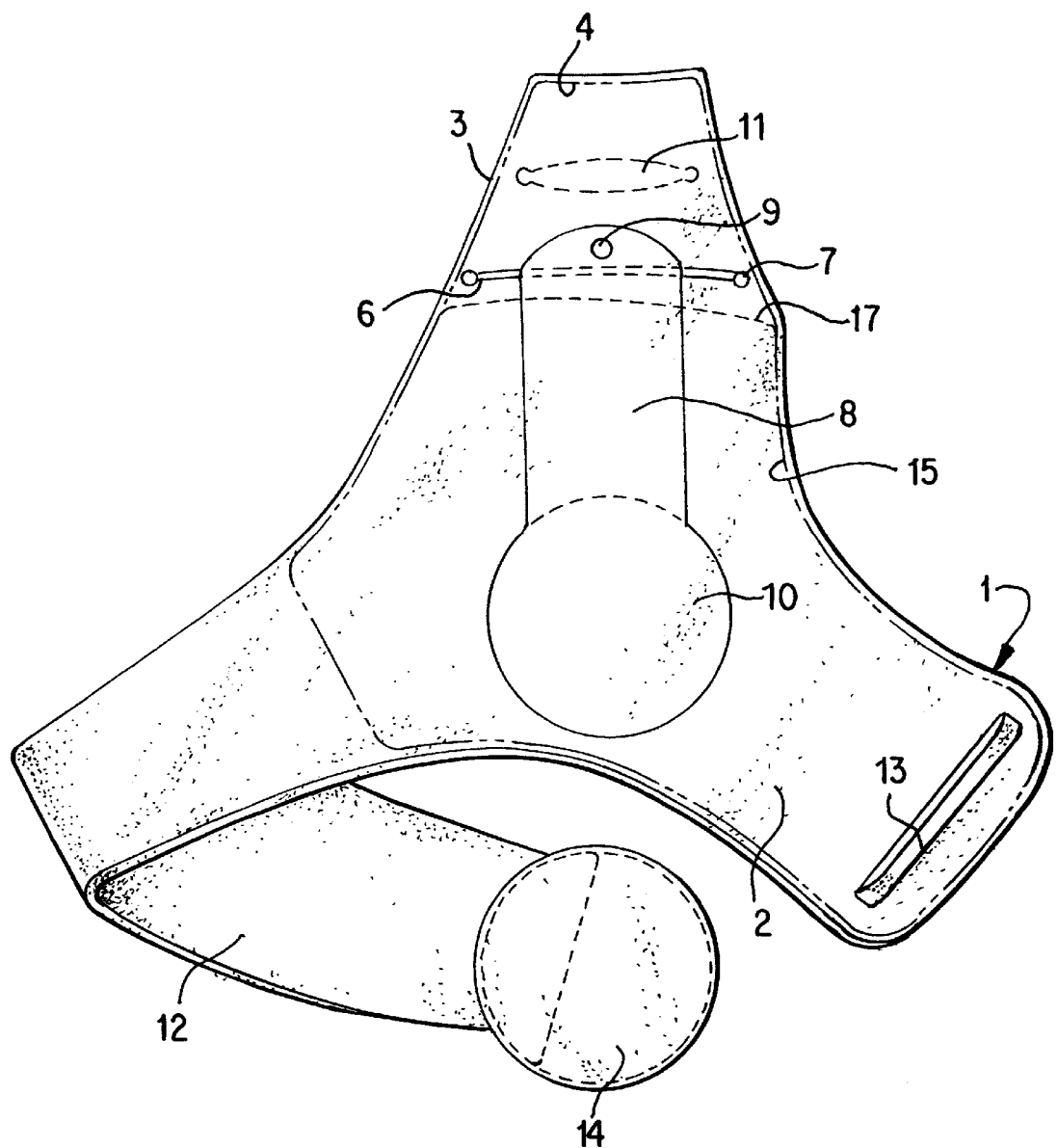
FIG. 2 shows the same orthesis in the manner of a layout, in a top view of the flap bridging the transverse slit.

FIG. 2 shows the orthesis 1 in the manner of a layout, specifically in a top view of the flap 8, and the transverse slit 6 which, here, is virtually closed. Above the transverse slit 6, the oval marked by dashed lines indicates a transverse cutout 11 in the reinforcement 4, said cutout serving to make it possible for the reinforcement 4 to be pushed together if the thumb is bent as a result of a corresponding position of the end 10 of the flap 8, so that the reinforcement can oppose virtually no resistance to the bending of the thumb permitted by the position of the flap 8. The transverse cutout 11 is indicated, in FIG. 1, by the triangle 11 marked there.

FIG. 2 shows, furthermore, the belt 12, by means of which the wrist strap 2 can be secured to the wrist. The belt 12 loops round the hand somewhat above the wrist and is secured to the wrist strap 2 by being slipped through the eyelet 13, after looping round the hand, whereupon it is pressed onto the looping-round part of the belt 12 and fastened by means of a touch-and-close fastening. Here, the touch-and-close fastening is formed, on one side, by the hooked material 14 which, after being drawn through the eyelet 13, is pressed against that part of the belt 12 which slips through, said belt consisting of fleecy material on its outside.

Figure 3:
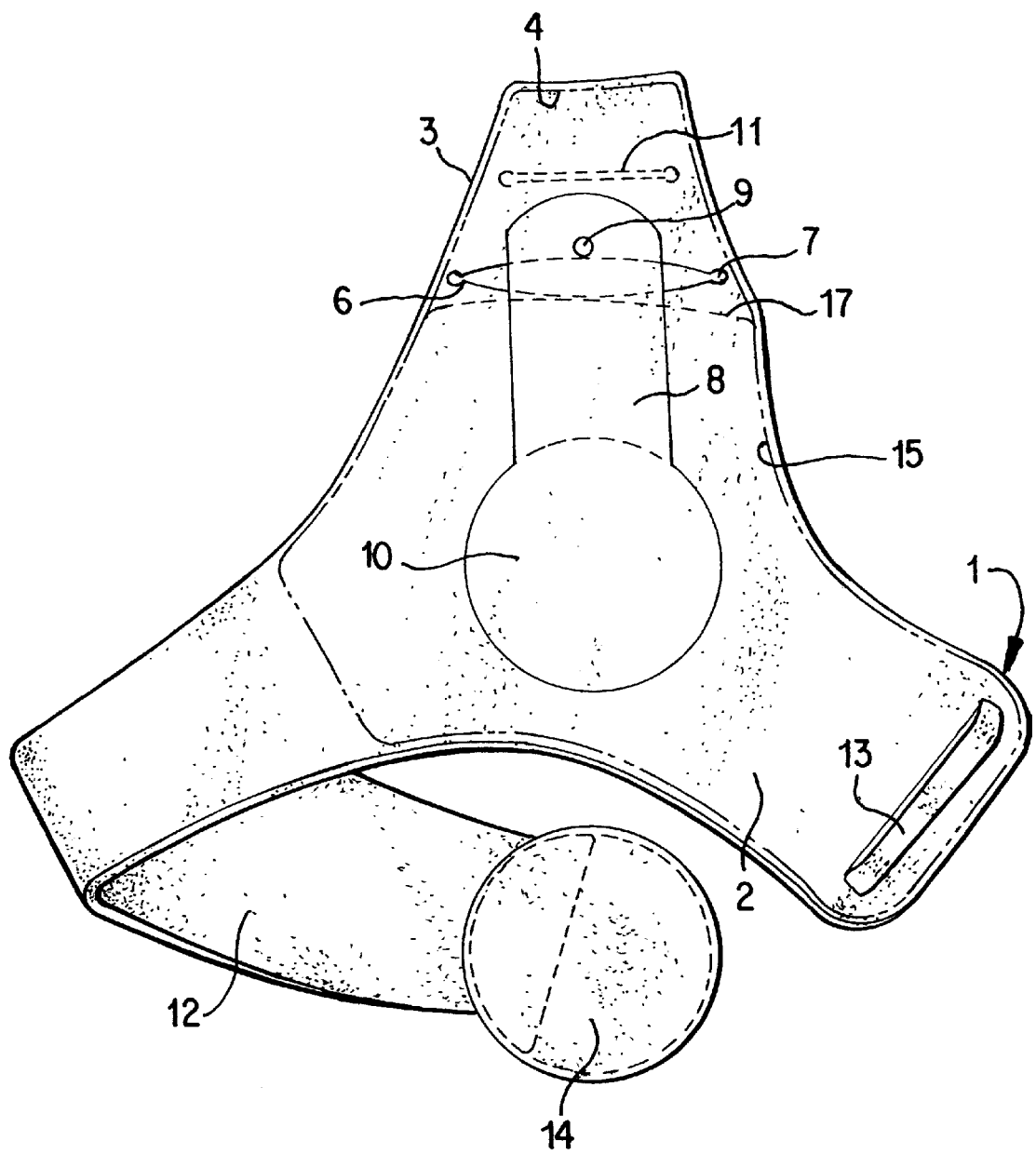
FIG. 3 shows the illustration according to FIG. 2 with the transverse slit opened.

FIG. 3 shows another view of the orthesis 1 which corresponds essentially to the illustration in FIG. 2, although the flap 8 is fastened with its end 10 to the wrist strap 2 in such a way that, when the flap 8 is in this position, the transverse slit 6 can open and consequently gives the thumb base joint a corresponding possibility of movement. When the extension piece 3 is in this position, the transverse cutout 11 is then compressed correspondingly.

So that the flap 8 can easily be secured with its end 10 to the wrist strap 2, the wrist strap 2 is provided, on its outside, with a coating made of fleecy material. The end 10 of the flap carries, on its side facing the wrist strap 2, the hooked material for a touch-and-close fastening which thus makes it possible for the end 10 and, consequently, the flap 8 to be secured selectively to the wrist strap 2.

So that the thumb to be treated is consequently given limited latitude of movement, if appropriate no latitude of movement at all, the wrist strap 2 and the flap 8 consist of essentially nonstretchable material. It should be pointed out, however, that an elastic material may also be provided, particularly for the flap, this affording the possibility, depending on the therapy, of giving the patient some latitude of elastic movement for his thumb.

As stated above, the extension piece 3 and the wrist strap 2 contain the reinforcement 4 (see the run of the dashed and dotted line). This reinforcement extends, here, both over the extension piece and over the essential part of the wrist strap 2, thus resulting in a firm support of the extension piece in relation to the wrist strap.

The dashed line 17 illustrated in FIGS. 2 and 3 represents the run of the extension piece 3 on its inside which is likewise designated by the same reference symbols in FIG. 1.

What is claimed is:

1. An orthesis, made of flexible material, for immobilizing the thumb base joint, comprising a wrist strap (2) adapted to surround the wrist and a tubular extension piece (3) adapted to receive the thumb, wherein the extension piece (3) contains a sheath-shaped reinforcement (4) with a transverse cutout (11) adapted to be located on the inside of the thumb base joint when the orthesis is received on a wrist, and in the region of the thumb base joint, on the outside of the thumb, a transverse slit (6) of a length such that the transverse slit (6) opens when the thumb base joint is bent, the degree of opening being limited by a flap (8) which, bridging the transverse slit (6), extends from the outer region of the extension piece (3) to the wrist strap (2) and can be secured to the latter.

2. The orthesis as claimed in claim 1, wherein the wrist strap (2) has, on its outside surface a coating of fleecy material of a touch-and-close fastening and the flap (8) is provided, on its inside surface, with hooked material for selective securing to the wrist strap.

3. The orthesis as claimed in claim 1 or 2, wherein the wrist strap (2), together with the extension piece (3), and the flap (8) consist of essentially nonstretchable material.

4. The orthesis as claimed in claim 1 or 2, wherein the flap (8) consists of elastic material.

5. The orthesis as claimed in claim 1, wherein the reinforcement (4) extends into the wrist strap (2) which is covered, on its outside surface, with the fleecy material and, on its inside surface, with a textile surface.

6. The orthesis as claimed in claim 1, wherein the wrist strap (2) terminates in a touch-and-close fastening (14).

7. The orthesis as claimed in claim 6, wherein the wrist strap (2) contains a belt (12) which can be secured selectively to the wrist strap (2) by means of an eyelet passing through said wrist strap.

* * * * *